(12) United States Patent
Clinthorne

(10) Patent No.: US 6,323,492 B1
(45) Date of Patent: Nov. 27, 2001

(54) METHOD FOR IMPROVING THE SPATIAL RESOLUTION OF A COMPTON CAMERA

(75) Inventor: Neal H. Clinthorne, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/423,822
(22) PCT Filed: May 15, 1998
(86) PCT No.: PCT/US98/09921
   § 371 Date: Feb. 3, 2000
   § 102(e) Date: Feb. 3, 2000
(87) PCT Pub. No.: WO98/52069
   PCT Pub. Date: Nov. 19, 1998

Related U.S. Application Data
(60) Provisional application No. 60/046,774, filed on May 16, 1997.

(51) Int. Cl.⁷ ...................................................... G01T 1/24
(52) U.S. Cl. ............... 250/394; 250/370.09; 250/370.01; 250/394; 250/363.03
(58) Field of Search ...................... 250/370.09, 370.01, 250/394, 363.03

(56) References Cited

U.S. PATENT DOCUMENTS
3,011,057 11/1961 Anger .

OTHER PUBLICATIONS
An Electronically Collimated Gamma Camera For Single Photon Emission Computed Tomography. Part 1: Theoretical considerations and Design Criteria, Med. Phys. 10(4), Jul./Aug. 1983, pp. 421–427, Manbir Singh.
A Novel Compton Scatter Camera Design for In–vivo Medical Imaging of Radiopharmaceuticals, 1995 IEEE vol. 3, pp. 1579–1583, Rohe, et al.
A Ring Compton Scatter Camera for Imaging Medium Energy Gamma Rays, IEEE Trans. On Nuclear Science, vol. 40, No. 4, Aug. 1993, Martin, et al.
Preliminary Characteristics of a Germanium–Based, Compton–Scatter Telescope, Trans. On Nuclear Science, vol. 36, No. 1, Feb. 1989, pp. 887–890, Piercey, et al.

*Primary Examiner*—Constantine Hannaher
*Assistant Examiner*—Andrew Israel
(74) *Attorney, Agent, or Firm*—Quarles & Brady, LLP

(57) ABSTRACT

A Compton camera has two detectors which each sense the location, energy and time of photon collisions. Compton events are detected in which a photon emanating from the subject collides with one detector at energy ($E_1$) and then the second detector at ($E_2$), both energies $E_1$ and $E_2$ are measured and used in conjunction with an initial photon energy $E_0$ to increase the resolution of the camera.

11 Claims, 7 Drawing Sheets

METHOD FOR IMPROVING THE SPATIAL RESOLUTION OF A COMPTON CAMERA

CROSS-REFERENCE TO RELATED APPLICATIONS

This application is a 371 of PCT/US98/09921 filed May 15, 1998 which claims benefit of Provisional No. 60/046,774 filed May 16, 1997.

STATEMENT REGARDING FEDERALLY SPONSORED RESEARCH

This invention was made with United States Government support Under Grant No. CA-32846 awarded by the National Cancer Institute. The Government has certain rights in the invention.

BACKGROUND OF THE INVENTION

The field of the invention is x-ray and gamma-ray cameras based on the Compton-scatter principle.

Scintillation cameras are widely used as diagnostic tools for analyzing the distribution of a radiation-emitting substance in an object under study, such as for the medical diagnosis of a human body organ. A typical scintillation camera of the Anger-type is described in U.S. Pat. No. 3,011,057.

The Anger-type scintillation camera can take a "picture" of the distribution of radioactivity throughout an object under investigation, such as an organ of the human body which has taken up a diagnostic quantity of a radioactive isotope. A scintillation camera of the Anger-type produces a picture of the radioactivity distribution by detecting individual gamma rays emitted from the distributed radioactivity in the object that pass through a collimator to produce a scintillation in a thin planar scintillation crystal. The scintillation is detected by a bank of individual photomultiplier tubes which view overlapping areas of the crystal Appropriate electronic circuits translate the outputs of the individual photomultiplier tubes into X and Y positional coordinate signals and a Z signal which indicates generally the energy of the scintillation event and is used to determine whether the event falls within a preselected energy window. A picture of the radioactivity distribution in the object may be obtained by coupling the X and Y signals which fall within the preselected energy window to a display, such as a cathode ray oscilloscope which displays the individual scintillation events as spots positioned in accordance with the coordinate signals. The detection circuitry typically provides for integrating a large number of spots onto photographic film.

The "resolution" of a scintillation camera refers to the ability of the camera faithfully to reproduce the spatial distribution of the radioactivity which is within the field of view of the device. The overall intrinsic resolution of the Anger camera detector is generally dependent on the ability of the detector to signal accurately the position coordinates of each scintillation event. In the Anger-type camera there is no way to determine the direction of the gamma ray which produced the scintillation event merely by detecting the location of the event. Instead, a collimator is placed in front of the detector to restrict to a narrow angle the direction of the gamma rays reaching the detector.

As a result of the need for a collimator to restrict the angle of the incident gamma rays, the Anger camera has a relatively low sensitivity, which is defined as that fraction of the gamma rays emanating from the source which actually reach the detector to produce an event that contributes to the image. If the collimator is less restrictive to admit more gamma rays and increase sensitivity, the spatial resolution of the camera is reduced.

Another type of camera relies on the Compton effect to determine the angle of incidence of a gamma ray. This camera does not require a collimator in order to determine gamma ray angle of incidence and a very efficient camera is, therefore, possible. The operating principle of a Compton camera is described by Martin JB, Knoll GF, Wehe DK, Dogan N, Jordanov V, Petrick N: A Ring Compton-scatter Camera For Imaging Medium Energy Gamma Rays, IEEE Trans. Nucl. Sci., 1993; 4-:972–978; and Singh M: Electronically Collimated Gamma Camera For Single Photon Emission Computed Tomography, Part I: Theoretical Considerations and Design Criteria, Med. Phys., 1983; 10(4) :421–427.

FIG. 1 shows a scatter aperture for a Compton camera which is composed of two detectors D1 and D2. Incident X- or γ-ray photons interact in the first detector D1 via Compton-scattering, and the scattered photon is detected in time-coincidence in the second detector D2. Using the measurements of the energy deposited in the two detectors, and location of D1 and D2, the direction of the incident photon can be resolved to within a conical ambiguity. Alternatively, if the energy of the incident photon is known, a measurement from only one of the two detectors is needed. By collecting a large number of these interactions and subsequent data processing, the conical ambiguity can be reduced and the source intensity of incident photons recovered. The primary attraction of Compton-scatter apertures for single-photon imaging is that they potentially offer reduced counting noise or improved spatial resolution. The potential for this improvement exists because the solid-angle efficiency of a scatter-camera can be two orders of magnitude higher than a conventional mechanically-collimated system for equal spatial resolution.

Despite the large gains in raw counting efficiency, some advantage is lost in the process of recovering the source distribution by removing the intrinsic ambiguity. Further reductions in performance—especially for imaging photons having energies below 200 keV—can arise from detectors having modest energy resolution. In a Compton-scatter camera, poor energy resolution translates directly to poor spatial resolution (and large noise amplification if this blurring is unfolded).

In mechanical collimated systems, efficiency must always be traded off against spatial resolution. High resolution necessarily means poor sensitivity. This is not the case for a Compton camera. Any method of reducing the uncertainty in the direction of the scattering angle that does not reduce efficiency will improve resolution. Using detectors having better energy resolution is one way to accomplish this. "Conventional" Compton cameras employ one detector having good energy resolution and another with only modest resolution. Measurements from both detectors are typically used to determine the incident energy $E_0$. Once the incident energy has been estimated, the measurement from the detector having the best energy resolution ($E_1$ or $E_2$) is used to estimate the scattering angle.

BRIEF SUMMARY OF THE INVENTION

The present invention is an improvement for a Compton camera which increases its spatial resolution by reducing the uncertainty of the scattering angle. More particularly, the present invention is a camera which includes a first detector (D1) for detecting the time, location and energy (E1) of photon collisions; a second detector (D2) for detecting the time, location and energy (E2) of collisions with photons emanating from the first detector (D1); a Compton event detector; and an angle detector for determining the angle of Compton scattering based on the energies $E_1$, $E_2$ and an estimation of energy $E_0$ of the photons emanating from the subject. The location and angle information for each Compton event is used by an image reconstruction means to produce an image.

A general object of the invention is to improve the spatial resolution of a Compton camera. The present invention reduces the angular uncertainty of the incident photon by using two detectors having high energy resolution in conjunction with knowledge of the energy spectrum of the incident photons. Where the incident energy spectrum is known exactly, the present invention can reduce the uncertainty in the scattering angle by up to a factor of $\sqrt{2}$ over the best single measurement. The maximum reduction occurs when two detectors D1 and D2 having equal energy resolutions are employed. If detectors having unequal energy resolutions are used the uncertainty $\sigma_E$ is given by $$\sigma_E = \sqrt{\frac{\sigma_1^2 \sigma_2^2}{\sigma_1^2 + \sigma_2^2}} \quad (1)$$

where $\sigma_1^2$ and $\sigma_2^2$ are the variances in the energy uncertainties for the first and second detectors, respectively. While $\sqrt{2}$ may seem like a small gain in spatial resolution, the pixel-wise variance in reconstructed images, as a function of spatial resolution, can be quite non-linear. Small resolution changes can, therefore, result in relatively larger variance changes in the intensity estimate at each image pixel.

In one embodiment the camera includes a third detector (D3) for detecting the time, location and energy (E3) of collisions between said third detector (D3) and photons emanating from the second detector (D2); and the angle determining means is also responsive to the energy (E3) to calculate the angle of Compton scattering.

In one embodiment the angle determining means calculates the angle $\phi$ of Compton scattering according to the expression:

$$(\hat{\varphi}, \hat{E}_0, \hat{X}_1) = \underset{(\varphi, E_0, X_i)}{\mathrm{argmax}} f(\varphi, E_0, X_1 \mid \{Y_i\}, \{t_i\}, \{X_i\})$$

where $X_1$ is the point of impact on the first camera and $f(\phi, E_0, X_i | \{Y_i\}, \{t_i\}, \{X_i\})$ is given by equation:

$$C \times \int \cdots \int \left[ \prod_{i=1}^{N} f(Y_i \mid E_j) f(t_i \mid \tau_i) \right] f(\{E_i\}, \{\tau_i\}, \{X_i\} \mid E_0, \varphi) dE_i d\tau_i$$

In another embodiment the angle determining means chooses an incident energy estimate $E_0$ as $Y_1+Y_2$ where $Y_1$ and $Y_2$ are measured energies corresponding to $E_1$ and $E_2$ and the determining means calculates the angle of the Compton scattering by first estimating energy $E_1$ using energies $Y_1$ and $Y_2$ and estimate $E_0$ and then using the $E_1$ estimate to determine the scattering angle $\phi$.

The determining means may preferably estimate energy $E_1$ by solving the following equation:

$$\hat{E}_1 = (\sigma_{D1}^2 + \sigma_{D2}^2)^{-1} [\sigma_{D2}^2 Y_1 + \sigma_{D1}^2 (\hat{E}_0 - Y_2)].$$

Wherein Doppler broadening (explained below) is negligible the determining means preferably estimates angle $\phi$ by solving the following equation:

$$\hat{\varphi} + \cos^{-1}\left[\frac{\alpha}{\hat{E}_0} - \frac{\alpha}{\hat{E}_0 - \hat{E}_1} + 1\right]$$

where: $\alpha = \frac{E_0}{m_0 c^2}$ and where $m_0 c^2$ is the rest mass of an election.

Where Doppler broadening is significant the determining means calculates the angle of the Compton scattering by solving the following equation:

$$\hat{\varphi} = \underset{\varphi}{\mathrm{argmax}} f(\hat{E}_0, \hat{E}_1 \mid \varphi).$$

The invention also includes a method for use with the above referenced camera wherein the method comprises the steps of detecting the time, location and energy (E1) of collisions between said first detector (D1) and photons emanating from the subject, detecting the time, location and energy (E2) of collisions between said second detector (D2) and photons emanating from the first detector (D1), identify pairs of collisions in the respective first and second detectors that are produced by Compton events by analyzing the detected information, calculating the angle of Compton scattering of said detected Compton event as a function of energies E1 and E2 produced by a detected Compton event and an estimation of the energy $E_0$ of said photons emanating from the subject and producing an image as a function of the location information produced by each detected Compton event and the corresponding calculated Compton scattering angle to produce said image.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DETAILED DESCRIPTION OF THE INVENTION

Figure 1:
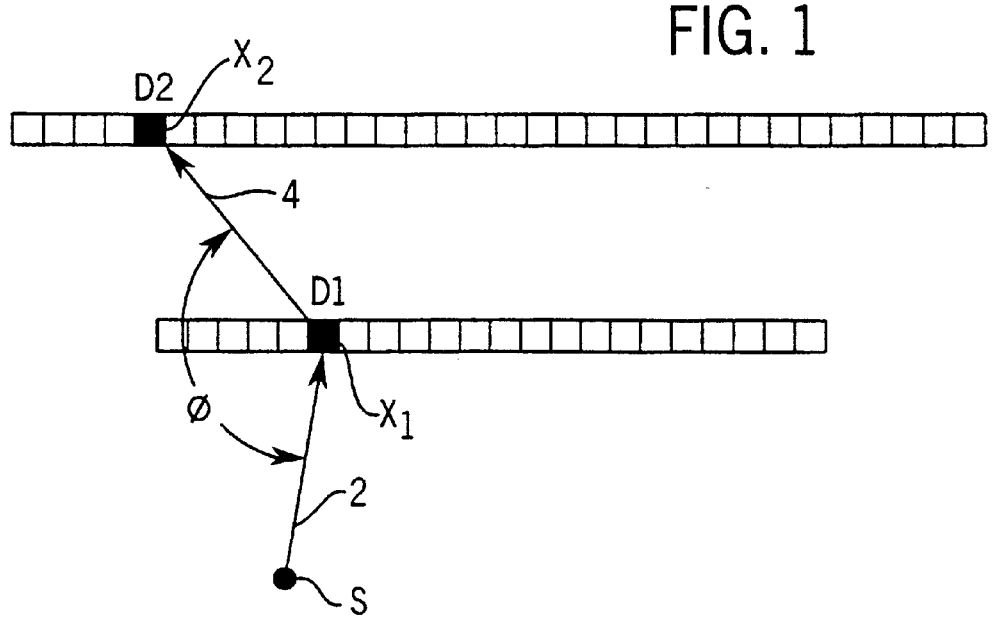
FIG. 1 is a schematic representation of a Compton-scatter aperture which employs two detectors.

Referring now to the drawings and specifically to FIG. 1, two detectors D1 and D2 are positioned in parallel relationship to one side of a source S. detector D1 between source S and detector D2. A gamma particle produced by source S having an initial energy $E_0$ travels along the path indicated by arrow 2 impacting detector D1 at point $X_1$. Upon impact, some of the particles energy $E_1$ is absorbed by detector D1 and the particle is deflected exiting detector D1 along the path indicated by arrow 4 toward detector D2 with the remaining energy $E_2$ (i.e. $E_0-E_1$). The particle impacts detector D2 at point $X_2$. A scatter angle between arrows 2 and 4 is indicated by symbol $\phi$.

For the purposes of this explanation the measurements of the photon energies recorded in detectors D1 and D2 will be referred to by symbols $Y_1$ and $Y_2$, respectively. Assuming measurements $Y_1$ and $Y_2$ are independent, a posterior probability density for the deposited energies $E_1$ and $E_2$ given measurements $Y_1$ and $Y_2$ can be expressed as:

$$f(E_1,E_2|Y_1,Y_2)=C \times f(Y_1|E_1)\ f(Y_2|E_2)f(E_1,E_2|E_0) \quad (2)$$

where C is a normalization constant.

Because energy is conserved upon detection, the following general conservation of energy equation can be written:

$$E_0=E_1+E_2 \quad (3)$$

Equations (2) and (3) can be combined to yield:

$$f(E_1,E_2|Y_1,Y_2)=C \times f(Y_1|E_1)\ f(Y_2|E_0-E_1)f(E_1|E_0)f(E_0) \quad (4)$$

Note that the prior density on energies $E_1$ and $E_2$ in Equation 2 has been split into the product of two terms. The first term describes the conditional probability of depositing energy $E_1$ in detector D1 given incident energy $E_0$. Its relation to the Klein-Nishina formula (see Equation 7 below) will become clear below. It also depends to a lesser extent on the geometry of detectors D1 and D2 and the detector fields-of-view. For example, for a point source and small detectors, only one scattering angle would be possible, and $f(E_1|E_0)$ would reflect this. The prior density on the incident energies $f(E_0)$ is simply the incident energy spectrum whose area has been normalized to unity.

In an equivalent expression the likelihood function can be written in terms of the incident energy $E_0$ and scatter angle $\phi$ in place of energies $E_1$ and $E_2$ as:

$$f(\phi,E_0|Y_1,Y_2)=C \times f(Y_1|E_0-g(\phi,E_0))f(Y_2|g(\phi,E_0))f(\phi|E_0)f(E_0); \quad (5)$$

where:

$$g(\varphi, E_0) = \frac{E_0}{1 + \frac{E_0}{m_0 c^2}(1 - \cos\varphi)} \quad (6)$$

and where $m_0 c^2$ is the rest mass of an election (511 keV) and $f(\phi|E_0)$ is essentially the Klein-Nishina formula normalized as a probability density function:

$$f(\varphi | E_0) = C \times \sin\varphi \times \left(\frac{1}{1 + \alpha(1 - \cos\varphi)}\right)^2 \left(\frac{1 + \cos^2\varphi}{2}\right) \times \left(1 + \frac{\alpha^2(1 - \cos\varphi)^2}{(1 + \cos^2\varphi)(1 + \alpha(1 - \cos\varphi))}\right); \quad (7)$$

in which:

$$\alpha = \frac{E_0}{m_0 c^2} \quad (8)$$

As noted above, $f(E_1|E_0)$ may deviate somewhat from this formula because of system geometry.

Given either of the posterior density functions expressed in Equations 4 or 5, an "optimum" estimator for the incident energy and scattering angle can be derived.

The maximum a posteriori estimate for energies $E_1$ and $E_0$ (equivalent as noted above to estimating $\phi$ and $E_0$) is:

$$(\hat{E}_0, \hat{E}_1) = \underset{E_0,E_1}{\operatorname{argmax}} \log f(Y_1 | E_1) + \\ \log f(Y_2 | E_0 - E_1) + \\ \log f(E_1 | E_0) + \log f(E_0) \quad (9)$$

If $f(E_0)$ describes a continuous spectrum (i.e. $f(E_0)$ contains no characteristic energy lines), Equation 9 can be solved by setting the gradient (with respect to $E_1$ and $E_0$) equal to zero with the appropriate choice of estimates $\hat{E}_1$ and $\hat{E}_0$ such that:

$$\nabla \log f(Y_1|\hat{E}_1) + \nabla \log f(Y_2|\hat{E}_0-\hat{E}_1) + \nabla \log f(\hat{E}_1|\hat{E}_0) + \nabla \log f(\hat{E}_0) = 0. \quad (10)$$

MAP estimation may be important in γ-ray astronomy applications where the incident spectrum can be measured with high accuracy and is sharply peaked at several locations.

The limiting variance for estimating $\hat{E}_1$ and $\hat{E}_0$ for any unbiased estimator is given by the global Cramèr-Rao (CR) bound as:

$$K(E_0,E_1) \geq [-E[\nabla^2(\log f(Y_1,Y_2|E_0, E_1) + \log f(E_1|E_0) + \log f(E_0))]]^{-1} \quad (11)$$

where the K is the covariance matrix for any estimator of $E_1$ and $E_0$. MAP estimators are important because they asymptotically (in the limit of a large number of observations) achieve the bound. Often they perform very well relative to the bound for far fewer observations.

Although MAP estimation provides perhaps the ultimate performance, it requires full knowledge of the incident energy spectrum or at least a probabilistic formulation if the incident spectrum has unknown characteristics. Usually, information of this detailed nature is not available; nevertheless, the incident spectrum often contains distinctive features. In particular, it may consist of a series of near δ-functions or lines having characteristic energies $E^{(k)}$. Denote the sequence of incident characteristic energy lines as $$\{E^{(k)}\}_{k=1}^{K}.$$

In addition to the characteristic or discrete spectrum there is usually a source of photons having a continuum of energies. The composite incident spectrum is the sum of these continuous and discrete spectrum contributions.

Often, it is only the discrete spectrum that is significant and background arising from the continuous spectrum is considered a nuisance. This is typical in nuclear medicine where a radionuclide may emit γ-rays at a single energy. Due to Compton-scatter in an object (e.g. a patient), however, the flux incident on the camera contains both photons having the characteristic energy, which are desirable, and scattered photons having a continuum of energies. Registration of this scattered radiation results in an undesirable background. For this case one must only decide whether or not an incident photon had an energy equal to one of the $E^{(k)}$ or not. Once an $E^{(k)}$ is selected (and there will be some error in classifying incident photons), it can be used as a hard constraint to reduce uncertainty in the scattering angle estimate.

Rather than starting off with a discussion of the spectral classification process, a simple estimator for scattering angle $\phi$ is developed under the assumption that the incident energy $E_0$ is known. The estimator does not use all information inherent in the measurement; and in particular, the prior probability density function (pdf) $f(E_1|E_0)$ is ignored. Under conditions normally encountered in medical imaging, the performance of estimators using this prior pdf would only be slightly better than the simpler estimator described next.

Assuming $E_0$ is known and ignoring the prior pdf allows a log-likelihood function for the observations, given energy $E_1$, to be written as:

$$\log f(Y_1, Y_2|E_0, E_1) = \log f(Y_1|E_1) + \log f(Y_2|E_0 - E_1) \quad (12)$$

For the purpose of this explanation only, assume that the individual terms are gaussian-distributed with variances $\sigma_{D1}^2$ and $\sigma_{D2}^2$ for detectors D1 and D2 respectively. Equivalently:

$$Y_i \sim N(E_i, \sigma_{Di}^2) \quad (13)$$

Assume also that the variances for detectors D1 and D2 are independent of energy. The maximum likelihood (ML) estimator for energy $E_1$ reduces to a simple least-squares problem as:

$$\hat{E}_1 = \frac{\sigma_{D2}^2 Y_1}{\sigma_{D1}^2 + \sigma_{D2}^2} + \frac{\sigma_{D1}^2 (E_0 - Y_2)}{\sigma_{D1}^2 + \sigma_{D2}^2}. \quad (14)$$

Equation 14 represents the ML estimator for gaussian distributed data with known variances. Typically, for any distribution, a similar generalized least-squares estimator can be derived where the weights are determined from the first- and second-moments of the likelihood functions. The weights derived from the variances may depend on either the data or the values of $E_0$ and $E_1$ making the estimator non-linear with respect to the data. As is clear in Equation 14 when the incident energy is $E_0$ assumed known, measurements from both detectors D1 and D2 can be used to reduce errors in the estimate of $E_1$ and hence in scattering angle $\phi$.

To compare the performance of an estimator using Equation 14 with performance of a typical Compton camera, equations which represent approximations for the variances $\sigma_\phi^2$ in scattering angle $\phi$ given the uncertainties in estimates $\hat{E}_0$ and $\hat{E}_1$ can be derived.

An equation for estimating the scattering angle $\phi$ from estimates of incident energy $E_0$ and energy $E_1$ absorbed by detector $D_1$ upon scattering is:

$$\varphi = \cos^{-1}\left(1 + \frac{\alpha}{E_0} - \frac{\alpha}{(E_0 - E_1)}\right) \quad (15)$$

This formula is valid when Doppler broadening of the Compton line width is inconsequential. Doppler broadening is explained below. Typical Compton cameras have used less than all information gathered to estimate the scattering angle $\phi$. For example, some cameras estimate the scattering angle using either the energy measurements $E_1$ and $E_2$ from the first and second detectors $D_1$ and $D_2$ while others use the incident energy $E_0$ and the energy measurement from one of the two detectors $D_1$ or $D_2$. While these cameras appear to be simple and therefore desirable, unfortunately the variance in the estimates generated by these cameras is relatively large.

The variance of the scattering angle estimate is approximated by linearizing the estimator for scattering angle and calculating the variance of the linearized estimator.

In the first case, where energies $E_1$ and $E_2$ are measured, $E_0$ is unknown and the prior pdf is neglected the energies deposited in detectors $D_1$ and $D_2$ can be estimated individually, which results in the following expression for variance $\sigma_{100}^2$, written in terms of $E_0$ and $E_1$:

$$\sigma_\varphi^2 \approx \frac{\alpha^2}{\sin^2\varphi}\left[E_0^{-4}\sigma_{DI}^2(E_1) + \left[\frac{1}{(E_0 - E_1)^2} - \frac{1}{E_0^2}\right]^2 \sigma_{D2}^2(E_0 - E_1)\right] \quad (16)$$

The fact that the variances can depend on the deposited energy has been denoted by $\sigma_D^2 = \sigma_D^2(E)$.

In the second case where $E_0$ is known and $E_1$ is measured, the variance is as follows:

$$\sigma_\varphi^2 \approx \frac{\alpha^2}{\sin^2\varphi}(E_0 - E_1)^{-4}\sigma_{DI}^2(E_1) \quad (17)$$

Alternatively, in the second case where $E_0$ is known and $E_2$ is measured, the variance is expressed as:

$$\sigma_\varphi^2 \approx \frac{\alpha^2}{\sin^2\varphi}E_2^{-4}\sigma_{D2}^2(E_2) \quad (18)$$

These expressions for angle variance $\sigma_\phi^2$ are well known in the Compton camera art.

When the present invention is used to improve the angular estimation and energy $E_0$ is known in advance, the energy measurements $E_1$ and $E_2$ from both detectors D1 and D2 can be used to reduce angular uncertainty based on the conservation of energy constraint (i.e. see Equation 3). To this end, the angular variance $\sigma_\phi^2$ using the present invention is expressed as follows:

$$\sigma_\varphi^2 \approx \frac{\alpha^2}{\sin^2\varphi}(E_0 - E_1)^{-4}\left[\frac{\sigma_{D1}^2(E_1)\sigma_{D2}^2(E_0 - E_1)}{\sigma_{D1}^2(E_1) + \sigma_{D2}^2(E_0 - E_1)}\right]. \quad (19)$$

The angular uncertainty always decreases when using two energy measurements since:

$$\frac{\sigma_{DI}^2(E_1)\sigma_{D2}^2(E_0 - E_1)}{\sigma_{DI}^2(E_1) + \sigma_{D2}^2(E_0 - E_1)} < \sigma_{DI}^2(E_1) \text{ and } \sigma_{DI}^2(E_0 - E_1) \quad (20)$$

As proof, by setting a value $\beta$ equal to $\sigma_{D1}^2(E1)/\sigma_{D2}^2(E_0 - E_1)$ (or vice-versa for detector D2) in Equation 20 and simplifying, we get:

$$\frac{1}{1+\beta}\sigma_{DI}^2 < \sigma_{DI}^2 \quad (21)$$

which holds for all $\beta > 0$ (the only possibility) because $(1\beta)^{-1} < 1$.

It is apparent that the variance improves the most over the best single measurement when $\sigma_{D1}^2 = \sigma_{D2}^2$. At this point the variance in the scattering angle is reduced by a factor of two, which results in resolution gains of 2 and $2\sqrt{2}$ in area and volume resolution, respectively. Note that if the energy resolution of one detector is much worse than that of the other as is the case in current Compton cameras, there will be virtually no improvement in angular uncertainty. However, it is a teaching of the present invention that by using modern solid-state detectors, it is reasonable to construct Compton-scatter apertures using two detectors having excellent energy resolution. One can thus achieve variance reductions closer to the maximum achievable factor of two for lower energy photons (<150–200 keV).

Figure 3:
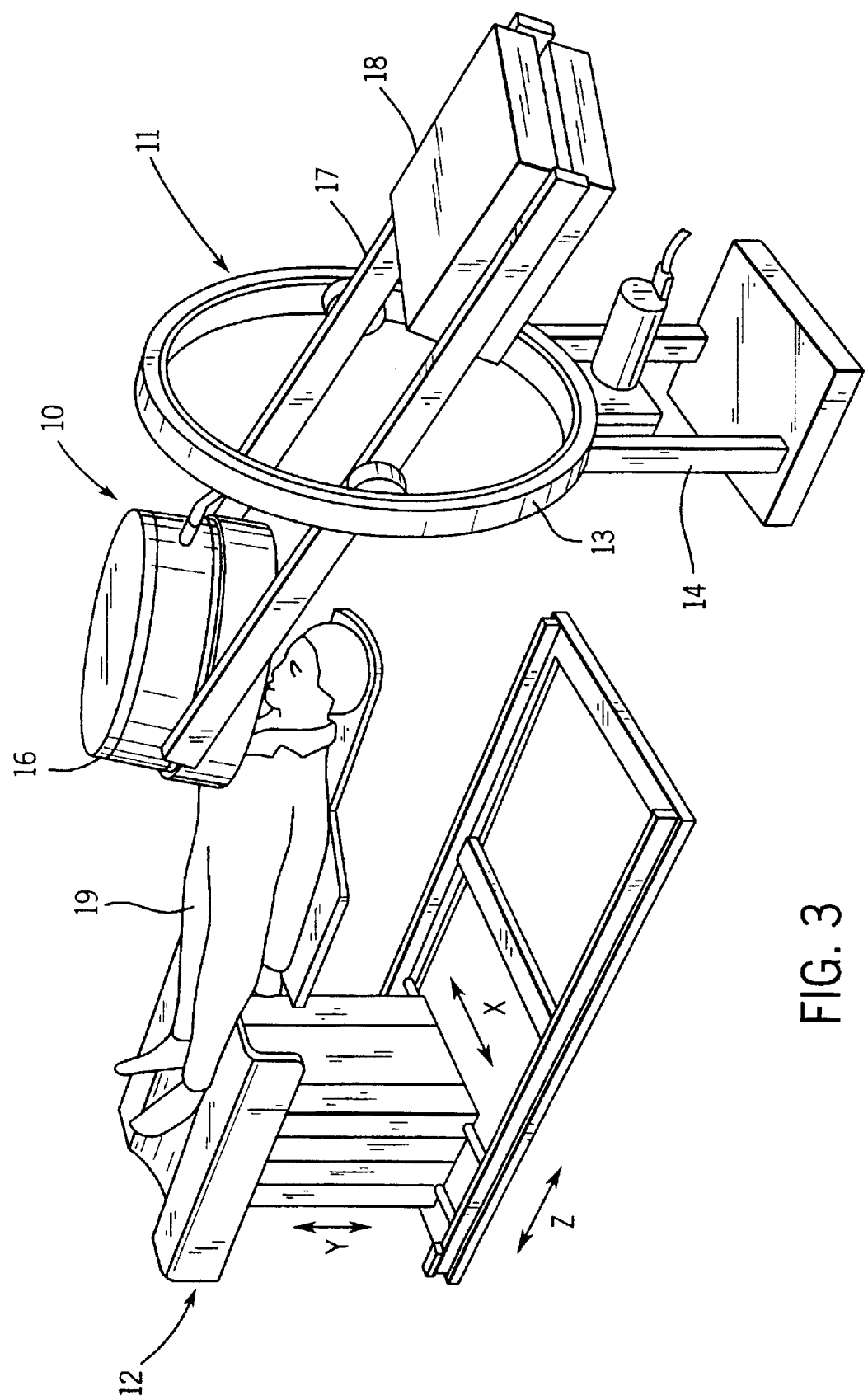
FIG. 3 is a pictorial view of a nuclear imaging tomographic scanning system which employs the present invention.

Referring to FIG. 3, there is shown generally at 10, a nuclear imaging tomographic scanning system which includes a tomographic scanner 11, and a patient support table 12. The scanner 11 comprises an annular gantry 13 supported in a vertical position as shown by a pedestal 14 and having a camera 16 supported from the gantry 13 in cantilevered fashion by an arm assembly 17 and balanced by a counterweight 18 on the other end of the arm assembly 17. The arm assembly 17 is so connected to the gantry 13 as to allow the entire arm assembly 17 to be rotated within the gantry 13 by a motor-drive system (not shown), to thereby rotate the camera 16 in a circular path to a variety of view angles around the patient 19 supported on the table 12. The movement of the camera 16 allows the collection of multiple views which can be used to reconstruct a tomographic image of the patient in the area of concern. The structure and operational movement of the scanner 11 is of a conventional nature.

Figure 4:
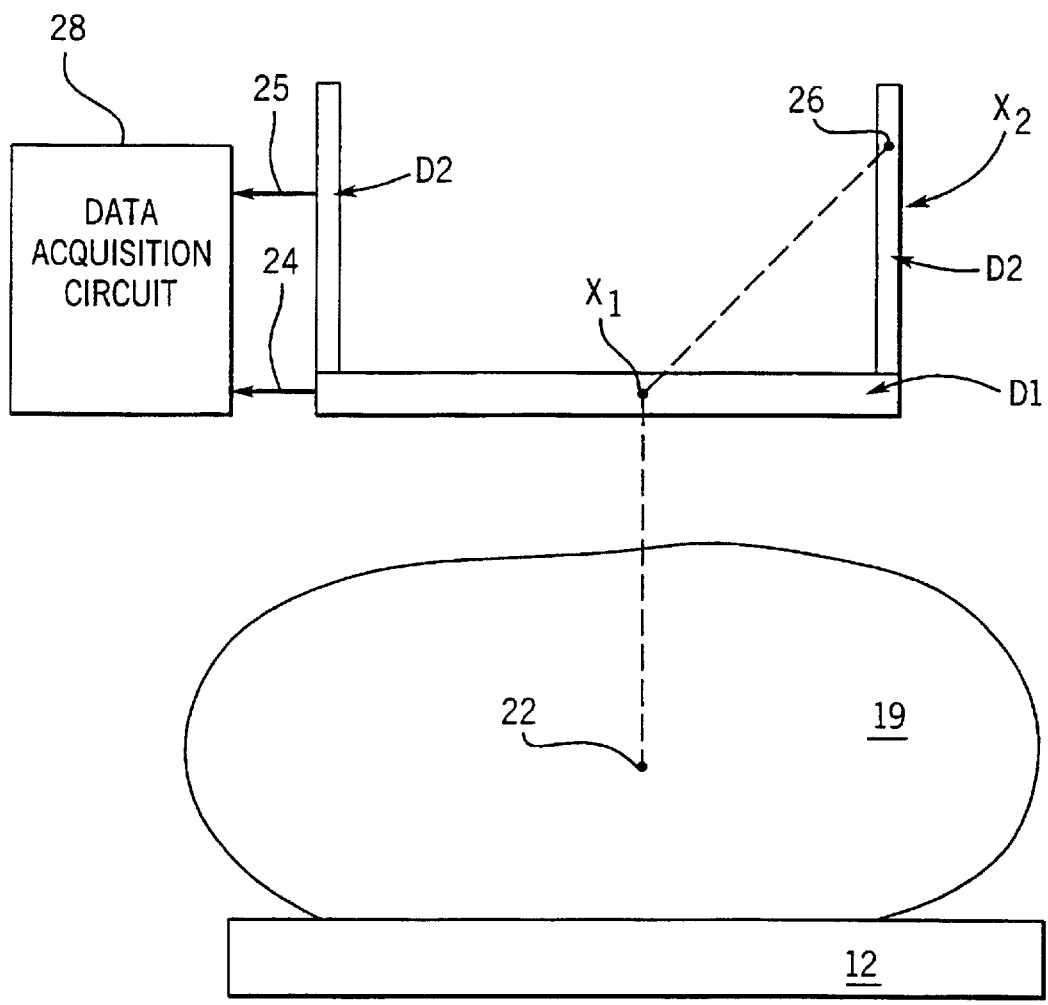
FIG. 4 is a schematic representation of the camera which forms part of the scanning system of FIG. 3.

Referring to FIGS. 3 and 4, as is well known in the art, the various isotopes used in nuclear medicine are preferentially absorbed by the patient 19 to emit gamma ray photons in a pattern which permits visualizing the configuration of body tissue and blood vessels. The camera 16 used to detect and locate the source of such emissions includes a first detector array D1 and a second detector D2 which abuts the outer perimeter of the first detector D1 and extends perpendicular therefrom.

A gamma ray emanating from a source location indicated at 22 and having energy $E_0$ passes into detector D1 and produces a Compton event at a location $X_1$ in the first detector D1. The gamma ray gives up energy $E_1$ during the Compton event and a gamma ray is emitted with energy $E_2$ from location $X_1$ which is absorbed at a location $X_2$ in the second detector D2. Detectors D1 and D2 produce signals indicative of sensed events, the signals provided to acquisition circuit 28 via data buses 24 and 25, respectively.

To generate required data (i.e. time of impact, energy absorbed, location of impact), each detector D1, D2 includes means for determining (1) the arrival time of each interaction $T_1$ and $T_2$, respectively, (2) the location $X_1$, $X_2$, respectively, of each interaction within the detector, and (3) the energy $E_1$, $E_2$, respectively, deposited during each interaction.

Detectors D1 and D2 preferably have similar energy resolutions. In a preferred configuration, scattering detector D1 is constructed of a material of low atomic number, which has low Doppler-broadening and a high probability that gamma-ray interactions will be Compton-scattering rather than photoelectric absorption or coherent scattering. Second detector D2 is constructed of a material having higher atomic number to increase the probability of photoelectrically absorbing the scattered radiation. In a typical situation, scattering detector D1 is constructed using a position-sensitive silicon detector while absorbing detector D2 employs germanium or cadmium zinc telluride.

Figure 8:
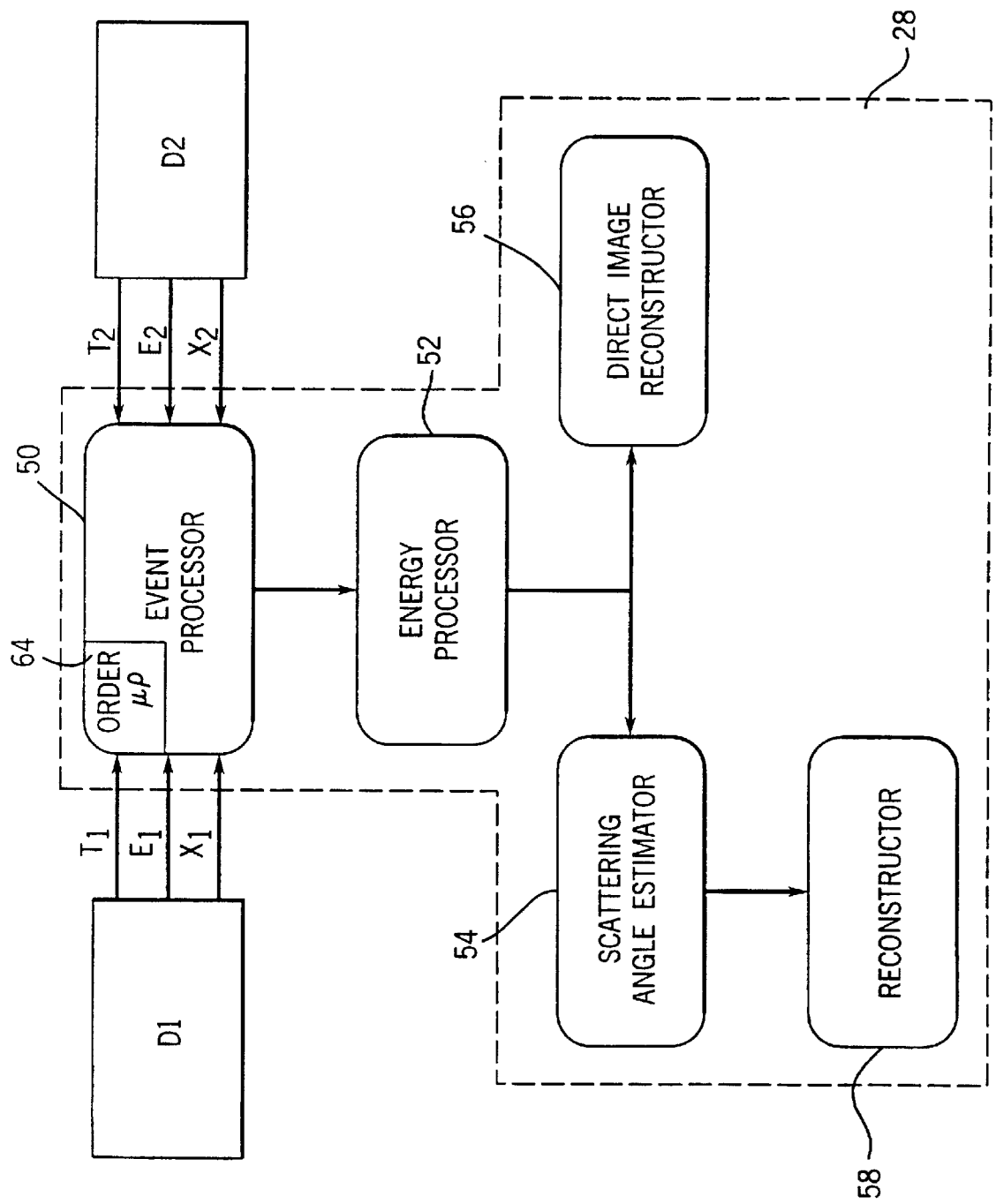
FIG. 8 is a block diagram illustrating hardware for implementing the inventive method.

Referring to FIGS. 4 and 8, circuit 28 comprises a plurality of components including an event processor 50, an energy processor 52, a scattering angle estimator 54, a first direct image reconstructor 56 and a second image reconstructor 58 which explicitly accounts for scatter angles. Each detector D1, D2 provides an arrival time estimate $T_1$, or $T_2$, a position $X_1$ or $X_2$, and an energy measurement $E_1$ or $E_2$ for each photon interaction to processor 50. Processor 50 first attempts to determine which set of detector interactions are associated with a particular gamma-ray incident on the Compton camera. For detector systems exhibiting good time resolution, this association is largely performed as it is currently done in positron emission tomography: If two (or more) interaction times fall within a short time-interval, they are assumed to have originated from the same gamma-ray photon incident on the Compton-camera.

The second task performed by processor 50 is to select the order of interactions. For example, Compton cameras are usually designed in such a way as to enhance the probability of scattering from detector D1 first. However, nothing prevents scatter from occurring in detector D2 first with subsequent interaction in detector D1 (or multiple interactions in D1 followed by D2). Processor 50 uses as its basis the likelihood function described by Equation 32. Specifically, processor 50 maximizes the likelihood term inside the integral by using estimates of arrival times, energies and interaction positions by using time, location and energy estimates to determine order of interaction, a more accurate result occurs. To this end, an ordering means or calculator 69 is provided in processor 50. In the alternative a suitable surrogate function could be used. For example, if the time resolution of each detector D1 and D2 is very good, the time measurements from each detector can be used to estimate the actual interaction times with very high fidelity. In this case, processor 50 really only needs to consider the arrival time measurements. Once the arrival times have been estimated the interaction order follows immediately.

Processor 50 formats the events into a time-ordered list, each element of the list corresponding to one (estimated) event incident on the Compton camera. Each list element further consists of a time-ordered sequence of detector positions and energies. For example, if the n-th gamma-ray incident on the camera interacted in detector D1 at position $X_1$ with measured energy $Y_1$ and the scattered photon interacted in detector D2 at $X_2$ with energy $Y_2$, the n-th element of the list would consist of two ordered pairs $[(Y_1,X_1), (Y_2,X_2)]$.

Each element of the list consists of N ordered pairs where N is the number of detected interactions associated with a single gamma-ray incident on the Compton-camera.

The resulting event list is first processed by energy processor 52 in order to estimate $E_0$. Typically, if both detectors have good energy resolution, the incident energy is estimated by first summing all measured energy corresponding to a single incident gamma-ray (or a single list element) according to the following for the case of two interactions:

$$E_{test} = Y_1 + Y_2 \qquad (22)$$

This estimate of $E_0$ is then compared with a relatively narrow energy window. If the event falls within the window then $\hat{E}_0$ is assigned a single energy corresponding to the characteristic energy of the gamma-ray emission of a radionuclide of interest.

As an example, consider 99m-Tc, which has a characteristic emission of approximately 140 keV. A narrow energy window on the Compton camera might run from a low of 139 keV to a high of 141 keV. If $E_{test}$ falls within the window then $\hat{E}_0$ is assigned the value of 140 keV regardless of the particular value of $E_{test}$.

Multiple energy windows can be accommodated and require multiple applications of the method described above. If the event falls within a desired energy window, the event is augmented with the initial energy estimate $\hat{E}_0$ and is passed on for further processing. If it does not fall in a desired energy range, it is removed from the list.

The list output from processor 52 may be processed in two ways. First, the scattering angles $\phi$ can be directly determined via estimator 54 from the measurements as described below and then passed on for image reconstruction using reconstructor 58. Second, the list can be passed directly to reconstructor 56 which applies a likelihood model for the camera system. While the second method retains more information and in theory is capable of providing better reconstructed images, the first method is usually sufficient. The invention is meant to cover both methods of reconstructing.

Where the scattering angle $\phi$ is estimated from two interactions and Doppler broadening is negligible (assuming the interaction order is D1→D2), the following formula is used:

$$\hat{E}_1 = (\sigma_1^2 + \sigma_2^2)^{-1}(\sigma_2^2 Y_1 + \sigma_1^2(\hat{E}_0 - Y_2)); \text{ and} \quad (23)$$

$$\hat{\varphi} = \cos^{-1}\left[\frac{\alpha}{\hat{E}_0} - \frac{\alpha}{\hat{E}_0 - \hat{E}_1} + 1\right]. \quad (24)$$

Similar formulae hold for the opposite interaction sequence and for more than two interactions. The estimated scattering angles as well as the location of the cone vertex (the position $X_1$ of the first interaction in the Compton-camera) is added to an output list and is passed on for reconstruction to reconstructer 58.

Figure 2:
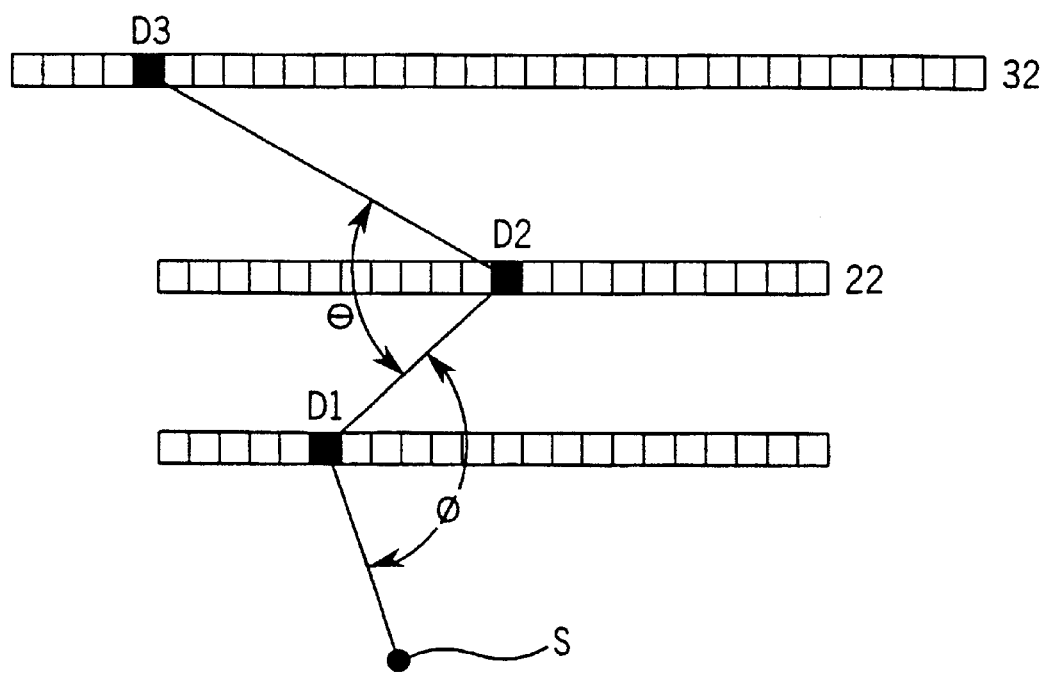
FIG. 2 is a schematic representation of a Compton-scatter aperture which employs three detectors.

The present invention can also be extended to cameras based on multiple-scattering. A two-scatter aperture system is shown in FIG. 2. Assume that the geometry of the three detectors is fixed such that $\theta$ is known. The MAP estimator can be developed in a manner analogous to the single-scatter case. To derive a similar estimator to that described above, start with the log-likelihood for observing detector outputs of $Y_1$, $Y_2$, and $Y_3$ given deposited energies $E_1$, $E_2$, and $E_3$:

$$\log f(Y_1,Y_2,Y_3|E_1,E_2,E_3) = \log f(Y_1|E_1) + \log f(Y_2|E_2) + \log f(Y_3|E_3) \quad (25)$$

Assuming that $E_0$ is known in addition to $\theta$ provides two constraint equations:

$$E_3 = E_0 - (E_1 + E_2) \quad (26)$$

and $$E_2 = g_\theta(E_0 - E_1) \overset{def}{=} (E_0 - E_1)\left[1 - \frac{1}{1 + \frac{E_0 - E_1}{\alpha}(1 - \cos\theta)}\right] \quad (27)$$

The corresponding constrained likelihood function is:

$$\log f(Y_1,Y_2,Y_3|E_1) = \log f(Y_1|E_1) + \log f(Y_2|g_\theta(E_0 - E_1)) + \log f(Y_3|E_0 - (E_1 + g_\theta(E_0 - E_1))) \quad (28)$$

Again, assuming the measurements are conditionally gaussian-distributed, the ML estimate of $E_1$ (hence the scattering angle $\phi$) satisfies $$\frac{\partial \log f}{\partial E_1} = \frac{(Y_1 - E_1)}{\sigma_{D1}^2} + \frac{\partial g_\theta}{\partial E_1}\frac{(Y_2 - g_\theta(E_0 - E_1))}{\sigma_{D2}^2} - \left(1 + \frac{\partial g_\theta}{\partial E_1}\right)\frac{(Y_3 - E_0 + E_1 + g_\theta(E_0 - E_1))}{\sigma_{D3}^2} = 0 \quad (29)$$

For the case where Doppler broadening is significant, there is no longer a one-to-one correspondence between the scattering angle and the incident energy and energy-loss in the first interaction. In this situation the scattering angle can be estimated by maximizing the appropriate likelihood function using $\hat{E}_0$ and $\hat{E}_1$ as estimated above and solving the following equation:

$$\hat{\varphi} = \underset{\varphi}{\text{argmax}}\, f(\hat{E}_0, \hat{E}_1 | \varphi). \quad (30)$$

The probability density function in Equation 30 can be calculated using methods well-known in the art.

Methods for reconstructing images from a Compton camera are well known with the better methods based upon maximizing a penalized likelihood objective (sometimes referred to as Bayesian methods). All methods either explicitly or implicitly require a model for the recorded measurements as a function of the underlying distribution of radiotracer in the object. With the appropriate choice of model, Compton camera reconstructions can be performed from as little as a scattering angle and cone-vertex for each event. At the other end of the spectrum, the reconstruction could process the outputs from the detectors directly to create an image based on the likelihood function of Equation 32 below.

Most of the estimates of scattering angle above assume that the gamma-ray Compton-scatters from a free-electron at rest. Knowing the energy deposited in the first interaction is equivalent to knowing the scattering angle $\phi$. As the incident gamma-ray energies decrease, this assumption becomes poorer. Electrons in the scattering detector, which are bound to individual atoms, possess considerable momentum. The scattering of gamma-rays from these electrons, whose momentum is unknown priori, is no longer described by Equation 15. Rather it is more accurate to assume there is a probabilistic relationship between angle $\phi$ and energy $E_1$. Denote the probability density function (pdf) describing this relationship as $f(\phi, E_1|E_0)$. The pdf expresses the additional uncertainty in scattering angle due to the unknown electron motion and energy. This uncertainty results in what has previously been referred to as Doppler-broadening of the Compton line-width.

If the order in which the scattering occurs (for example, D1→D2→D3, etc.) is known, the likelihood function for observing the measurements given the unknown parameters of the incoming gamma-ray (direction and energy) can be written as:

$$f(\varphi, E_0, X_1 | \{Y_1, \ldots, Y_N\}) = C \times \quad (31)$$

$$\int_{\varepsilon_1}\cdots\int_{\varepsilon_{N-1}} \prod_{i=1}^{N} f(Y_i | E_i) f\left(\left\{E_1, \ldots, E_{N-1}, E_0 - \sum_{j=1}^{N-1} E_j\right\}\bigg| E_0, \varphi\right) f(E_0, \varphi) dE_1 \ldots dE_{N-1}$$

where $X_1$ now denotes the location of the first interaction or the vertex of the cone of uncertainty from this relation. Equation 2 can be obtained as a special case when the relation between $\phi$, $E_1$, and $E_0$ is deterministic. Note that we have directly specified the likelihood for any number of scatters. In this case the scattering angle can be determined by maximizing Equation 31 given the measured data $Y_i$ or alternatively by simply maximizing the equation:

$$f\left(\left\{E_1, \ldots, E_{N-1}, E_0 - \sum_{j=1}^{N-1} E_j\right\} \middle| E_0, \varphi\right)$$

given estimates of $E_0$ and $E_1, \ldots, E_{N-1}$.

Generally, in the presence of this Doppler-broadening, the sequence in which the detectors are struck may not be as obvious as when this degradation is not present. The sequence can also be modeled in the likelihood function as follows.

$$f(\varphi, E_0, X_1 \mid \{Y_1\}, \{t_i\}, \{X_i\}) = \tag{32}$$

$$C \times \int \cdots \int \left[\prod_{i=1}^{N} f(Y_i \mid E_i) f(t_i \mid \tau_i)\right] f(\{E_i\}, \{\tau_i\}, \{X_i\} \mid E_0, \varphi)$$

$$f(E_0, \varphi) dE_i d\tau_i$$

where $Y_i$ and $t_i$ are the measured energies and arrival times, respectively. The true arrival times, energies, and positions are represented by $\tau_i$, $E_i$, and $X_i$. The terms inside the square brackets model the degradations due to the measurement system (e.g., detector noise). Although, we have only included energy and time, we could just as easily include measurement noise in the interaction position.

The second conditional probability density function is determined by the geometry of the Compton camera and by physical laws (including degradations such as Doppler broadening). The final term describes any prior knowledge regarding the spectrum of incident energies and scattering angles.

Note that in this formulation the positions of the interactions as well as the measured arrival times can be used to determine the appropriate sequence. As an example, the measured arrival times, positions and energies can be used to estimate the sequence of true interaction times $\{\tau_1, \ldots, \tau_N\}$ from which it is trivial to estimate the interaction order. The Event Processor described above can incorporate models based on the general likelihood formulation (6) in order to improve the classification of desired events (i.e., correct interaction order).

Figure 5:
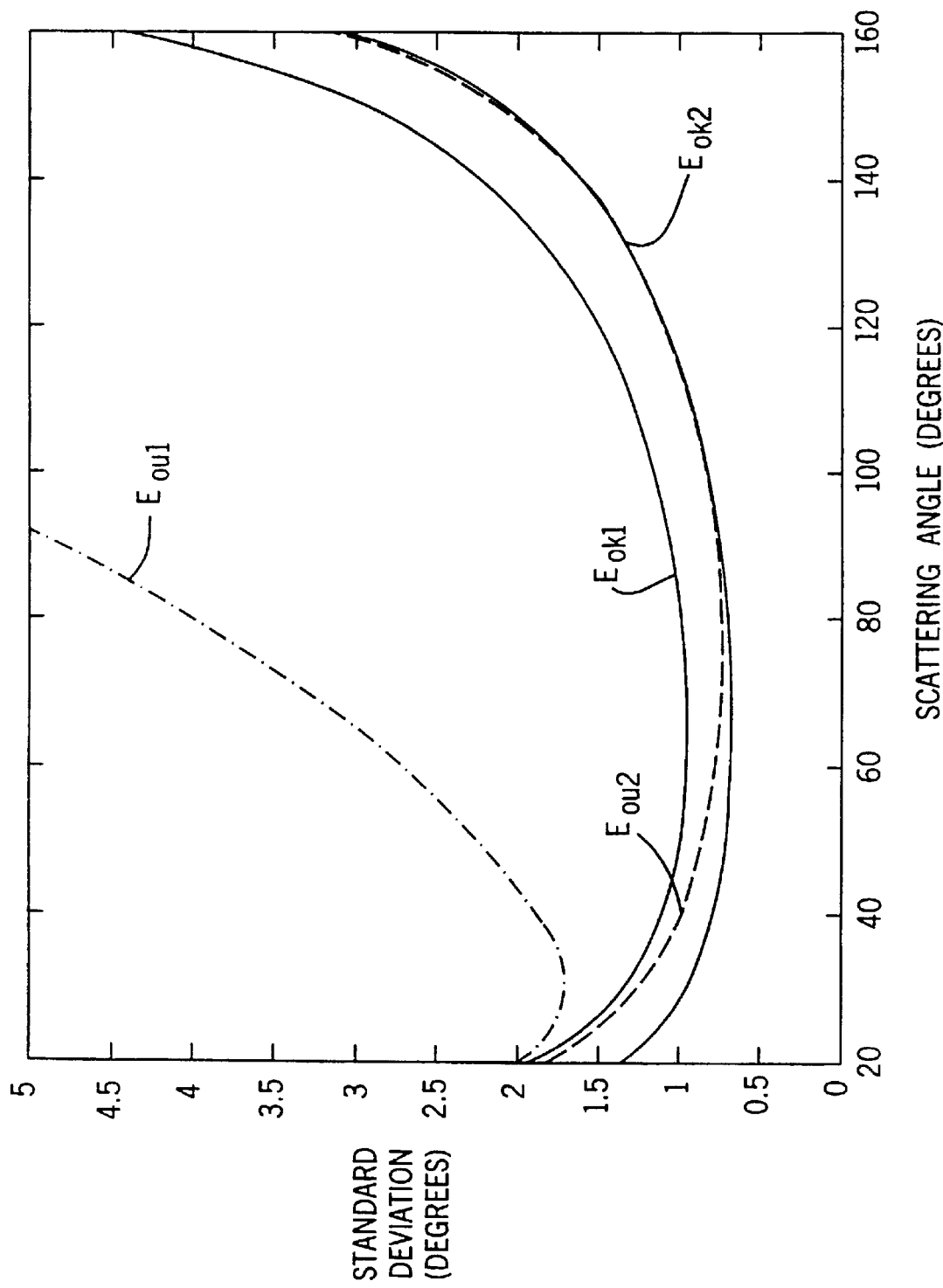
FIGS. 5–7 are graphic representations showing the advantages of the present invention when used in the scanning system of FIG. 3 with incident photon energies of 140, 80 and 364 keV, respectively.
Figure 6:
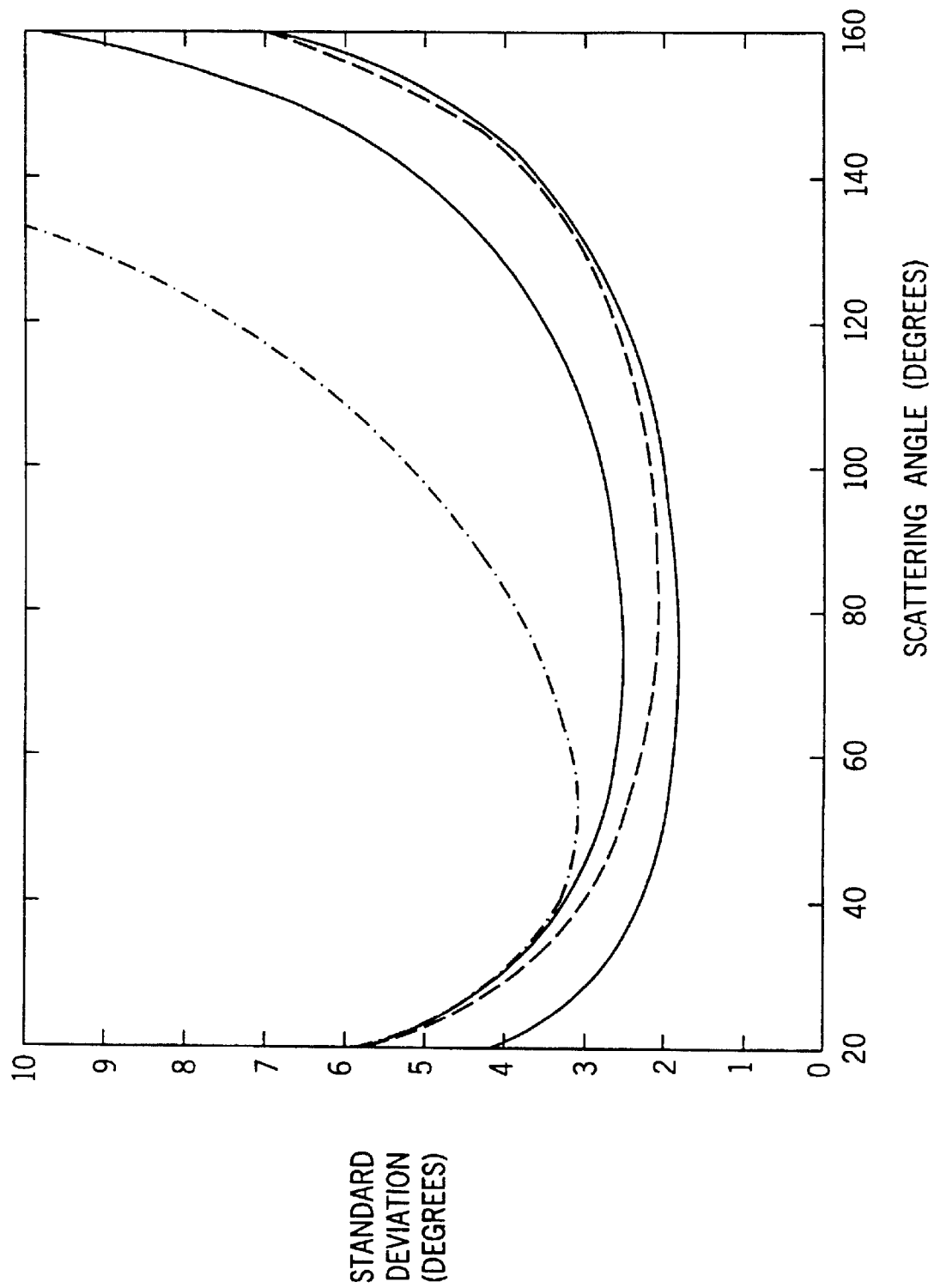
Figure 7:
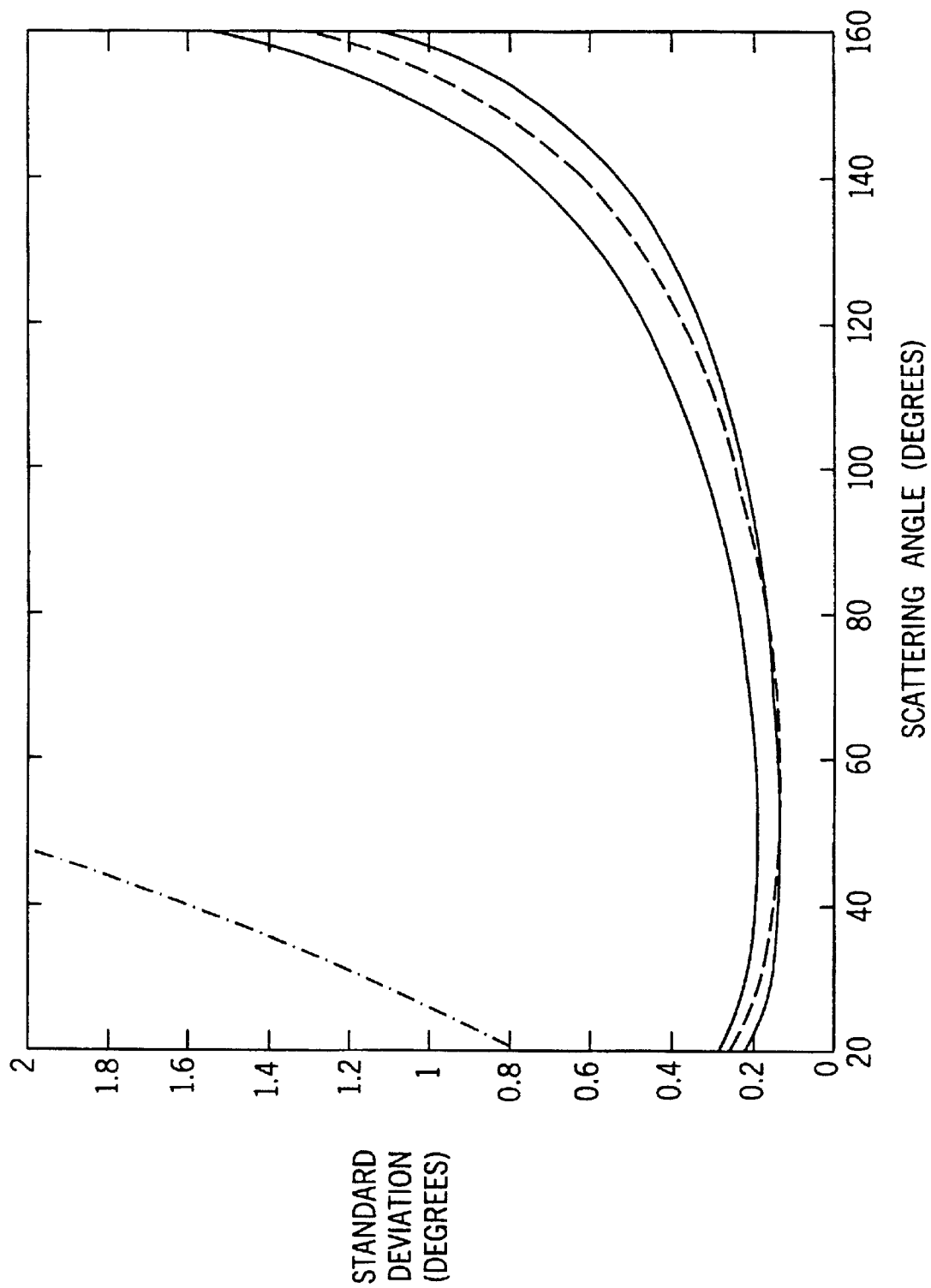

FIGS. 5–7 show plots of the three cases as a function of the scattering angle for incident photon energies of 140, 80, and 364 keV. In each of FIGS. 5 through 7 four curves are illustrated. A first curve $E_{ou1}$ represents the case where $E_0$ is initially unknown which results when the energy resolutions of detectors D1 of D2 are 1 keV FWHM and 10%, respectively. A second curve $E_{ou2}$ represents the case where $E_0$ is initially unknown when two high resolution detectors each having a 1 keV resolution, are used to determine scatter angle $\phi$. A third curve $E_{ok1}$ represents the case where $E_0$ is initially known and an energy measurement from only one (i.e. D1 or D2) of detectors D1 or D2, where the detector resolution is 1 keV, is used to determine scatter angle $\phi$. Fourth curve $E_{ok2}$ is related to the present invention and represents the case where $E_0$ is initially known, energy resolution of both detectors D1 and D2 is high and equal and energy measurements from both detectors D1 and D2 are used to determine scatter angle.

Clearly, where $E_0$ is unknown and an energy measurement from only a single detector is used to determine scatter angle (i.e. curve $E_{ou1}$) only limited performance results. When $E_0$ is known and only a single detector measurement is used (i.e. curve $E_{ok1}$), improved performance results. Assuming that the energy resolutions of both detectors are equal, and combining the measurements using Equation 14 gives the ultimate performance (i.e. curve $E_{ok2}$). When two high resolution detectors are used and the $E_0$ is not known in advance, performance (i.e. curve $E_{ou2}$) lies between that of the best single measurement and the optimum method. Apparently, this method can also take advantage of the improved resolution of both detectors. Nevertheless, at lower energies (80 and 140 keV) performance of the inventive method is significantly better over the angular range in which much of the scattering occurs (e.g. 0 to 90°).

To separate regions of the spectrum that contain the characteristic energies from continuum radiation, a narrow energy window is placed on an appropriately corrected sum of the detector outputs. The better the energy resolution of the sum of the two detectors, the better this separation can be accomplished.

Nothing is perfect, and inevitably some continuum radiation will contaminate the measurements of the characteristic energies. Since this radiation is by and large smoothly varying with respect to energy, however, its contribution to the characteristic energy windows can be estimated by placing windows that are somewhat wider to either side of these narrow windows. The contribution of the continuum radiation to the narrow window is estimated, and then either explicitly or implicitly removed. Wide windows decrease counting noise in the measurements at the expense of potential inaccuracy.

The corrected value from the k-th window is an estimate of the intensity of characteristic radiation having energy $E^{(k)}$. We assume that multiple characteristic energies are separated by intervals significantly larger than the energy resolution of the system so that cross-talk will be negligible.

At higher energies a fraction of the interacting photons may not be completely absorbed resulting in an energy of less than $E_0$ deposited within the camera. There are two alternatives for processing: either one can not register incomplete absorptions, selecting only those events that fall into the narrow window; or one can attempt to identify these lower energy events, which will now have a continuum of energies. In the first case, counting efficiency is reduced resulting in greater image noise. In the second, it may be difficult to separate desirable events from those that are not. Although an optimum separation can be accomplished in principle using a complete model for the likelihood function of the camera (Equation 32), performance may be highly susceptible to model inaccuracies.

It should be understood that the methods described above are only exemplary and do not limit the scope of this invention and various modifications could be made by those skilled in the art that would fall under the scope of the invention. To apprise the public of the scope of the this invention, we make the following claims:

What is claimed is:

1. A camera for creating an image of the radiation density of a source of photons located in a subject, the camera comprising:
   a first detector (D1) for detecting the time, location (X1) and energy (E1) of collisions between said first detector (D1) and photons emanating from the subject;
   a second detector (D2) for detecting the time, location (X2) and energy (E2) of collisions between said second detector (D2) and photons emanating from the first detector (D1);

Compton event detector means connected to the first and second detectors (D1 and D2) and being responsive to the information produced thereby to identify sets of collisions in the respective first and second detectors that are produced by Compton events; and image reconstruction means responsive to energies E1 and E2 produced by a detected Compton event and an estimation $\hat{E}_0$ of a photon incident energy for constructing an image;

angle determining means responsive to the energies E1 and E2 produced by a detected Compton event and an estimation of the energy $E_0$ of said photons emanating from the subject for calculating the angle of Compton scattering of said detected Compton event.

2. The camera as recited in claim 1 which includes a third detector (D3) for detecting the time, location and energy (E3) of collisions between said third detector (D3) and photons emanating from the second detector (D2); and the angle determining means is also responsive to the energy (E3) to calculate the angle of Compton scattering.

3. The camera as recited in claim 1 in which the angle determining means calculates the angle $\phi$ of Compton scattering according to the expression:

$$(\hat{\varphi}, \hat{E}_0, \hat{X}_1) = \arg\max_{(\varphi, E_0, X_1)} f(\varphi, E_0, X_1 \mid \{Y_i\}, \{t_i\}, \{X_i\})$$

where $X_1$ is the point of impact on the first camera and $f(\phi, E_0, X_1 | \{Y_i\}, \{t_i\}, \{X_i\})$ is given by equation:

$$C \times \int \cdots \int \left[ \prod_{i=1}^{N} f(Y_i \mid E_i) f(t_i \mid \tau_i) \right] f(\{E_i\}, \{\tau_i\}, \{X_i\} \mid E_0, \varphi) f(E_0, \varphi) dE_i d\tau_i$$

where C is a constant.

4. The camera of claim 1 wherein the angle determining means chooses an incident energy estimate $E_0$ as $Y_1+Y_2$ where $Y_1$ and $Y_2$ are measured energies corresponding to $E_1$ and $E_2$ and the determining means calculates the angle of the Compton scattering by first estimating energy $E_1$ using energies $Y_1$ and $Y_2$ and estimate $E_0$ and then using the $E_1$ estimate to determine the scattering angle $\phi$.

5. The camera of claim 4 wherein the determining means estimates energy $E_1$ by solving the following equation:

$$\hat{E}_1 = (\sigma_{D1}^2 + \sigma_{D2}^2)^{-1}[\sigma_{D2}^2 Y_1 + \sigma_{D1}^2(\hat{E}_0 - Y_2)]$$

where $\sigma_{D1}^2$ and $\sigma_{D2}^2$ are variances in the energy uncertainties for the first and second detectors, respectively.

6. The camera of claim 5 wherein Doppler broadening is negligible and wherein the determining means estimates angle $\phi$ by solving the following equation:

$$\hat{\varphi} + \cos^{-1}\left[\frac{\alpha}{\hat{E}_0} - \frac{\alpha}{\hat{E}_0 - \hat{E}_1} + 1\right]$$

where:

$$\alpha = \frac{E_0}{m_0 c^2}$$

and where $m_0 c^2$ is the rest mass of an election.

7. The camera of claim 5 wherein Doppler broadening is significant and the determining means calculates the angle of the Compton scattering by solving the following equation:

$$\hat{\varphi} = \arg\max_{\varphi} f(\hat{E}_0, \hat{E}_1 \mid \varphi).$$

8. A camera for creating an image of the radiation density of a source of photons located in a subject, the camera comprising:

a first detector (D1) for detecting the time, location and energy (E1) of collisions between said first detector (D1) and photons emanating from the subject;

a second detector (D2) for detecting the time, location and energy (E2) of collisions between said second detector (D2) and photons emanating from the first detector (D1);

Compton event detector means connected to the first and second detectors (D1 and D2) and being responsive to the information produced thereby to identify pairs of collisions in the respective first and second detectors that are produced by Compton events;

image reconstruction means responsive to the energies E1 and E2 produced by a detected Compton event and an estimation of the energy $E_0$ of said photons emanating from the subject for forming an image;

whereby, by being responsive to each of energies E1, E2 and $E_0$, image accuracy is increased as photon scattering angles related to energies E1, E2 and $E_0$ and implicit in the image are relatively more accurate.

9. The camera of claim 8 wherein the image reconstruction means further includes an angle determining means responsive to the energies E1, E2 and $E_0$ for calculating the angle of Compton scattering of said detected Compton event, the reconstruction means responsive to the scattering angle for each event when producing the image.

10. The camera of claim 8 wherein the event detector also includes an ordering means for determining the order of detector collisions for a Compton event wherein the ordering means determines the order of events as a function of the time, location and energy of each collision.

11. A method for use with a camera for creating an image of the radiation density of a source of photons located in a subject, the camera including first and second photon detectors, the method comprising the steps of:

detecting the time, location and energy (E1) of collisions between said first detector (D1) and photons emanating from the subject;

detecting the time, location and energy (E2) of collisions between said second detector (D2) and photons emanating from the first detector (D1);

identify pairs of collisions in the respective first and second detectors that are produced by Compton events by analyzing the detected information;

calculating the angle of Compton scattering of said detected Compton event as a function of energies E1 and E2 produced by a detected Compton event and an estimation of the energy $E_0$ of said photons emanating from the subject; and producing an image as a function of the location information produced by each detected Compton event and the corresponding calculated Compton scattering angle to produce said image.

* * * * *